United States Patent
Jones, Jr. et al.

(10) Patent No.: US 6,435,181 B1
(45) Date of Patent: Aug. 20, 2002

(54) RESPIRATORY MASK WITH ADJUSTABLE EXHAUST VENT

(75) Inventors: Allan R. Jones, Jr., Derry; Richard J. Kocinski, North Huntingdon, both of PA (US)

(73) Assignee: Sunrise Medical HHG Inc., Longmont, CO (US)

(*) Notice: Subject to any disclaimer, the term of this patent is extended or adjusted under 35 U.S.C. 154(b) by 0 days.

(21) Appl. No.: 09/563,682

(22) Filed: May 3, 2000

Related U.S. Application Data

(60) Provisional application No. 60/151,588, filed on Aug. 30, 1999.

(51) Int. Cl.$^7$ .............................................. A61M 16/00
(52) U.S. Cl. ............................ 128/204.18; 128/206.12; 128/206.21; 128/206.28; 128/206.18
(58) Field of Search ............................ 128/204.18, 848, 128/863, 201.15, 205.11, 206.15, 206.18, 206.28, 207.12, 207.13, 206.12, 206.21

(56) References Cited

U.S. PATENT DOCUMENTS

| | | | | |
|---|---|---|---|---|
| 3,256,910 A | * | 6/1966 | Cupp .................... | 128/207.12 |
| 3,889,671 A | * | 6/1975 | Baker .................... | 128/207.12 |
| 4,192,301 A | * | 3/1980 | Hardwick .............. | 128/205.17 |
| 4,919,128 A | | 4/1990 | Kopala et al. ......... | 128/207.18 |
| 5,477,852 A | | 12/1995 | Landis et al. .......... | 128/207.18 |
| 5,657,752 A | | 8/1997 | Landis et al. .......... | 128/207.13 |
| D402,755 S | | 12/1998 | Kwok .................... | D24/110.4 |
| 5,921,239 A | * | 7/1999 | McCall et al. ......... | 128/205.25 |
| 5,937,851 A | * | 8/1999 | Serowski et al. ...... | 128/202.27 |
| 6,044,844 A | | 4/2000 | Kwok et al. ........... | 128/207.11 |

FOREIGN PATENT DOCUMENTS

| | | |
|---|---|---|
| WO | WO 98/04310 | 2/1998 |
| WO | WO 98/34665 | 8/1998 |

* cited by examiner

*Primary Examiner*—Aaron J. Lewis
*Assistant Examiner*—Mital Patel
(74) *Attorney, Agent, or Firm*—MacMillan, Sobanski & Todd, LLC

(57) ABSTRACT

A nasal mask for use in respiratory therapy is provided with one or more vent ports which are adjustable for directing vented air in a direction which is most comfortable to the patient. By providing adjustable vent ports, the patient can adjust the direction of the vented air to a position that best accommodates the patient. Each vent port can be in the form of a passage in a member which is mounted to rotate in an opening through the mask. The member may be rotated in the opening to change the direction of air flowing through the passage or passages. The member may be designed to rotate about a fixed axis relative to the mask, or it may be spherical and designed to rotate in any direction. Preferably, a knob or tab is provided for grasping to facilitate manually adjusting the vent port orientation.

18 Claims, 5 Drawing Sheets

RESPIRATORY MASK WITH ADJUSTABLE EXHAUST VENT

CROSS-REFERENCE TO RELATED APPLICATIONS

This application claims the benefit of U.S. Provisional Application No. 60/151,588, filed on Aug. 30, 1999.

BACKGROUND OF THE INVENTION

This invention relates generally to an apparatus for use in treating sleep apnea and other respiratory disorders. More specifically, this invention relates to a nasal mask that provides septal support and permits nasal breathing.

Nasal masks which fit over a patient's nose are frequently used for respiratory therapy. For example, when treating sleep apnea and certain other respiratory disorders, a nasal mask is used to apply a continuous positive airway pressure (CPAP) through a patient's nasal passages. The positive pressure acts as a pneumatic splint which prevents collapse of the patient's airway. Throughout the treatment, the positive pressure is maintained in the airway as the patient is breathing. The masks also may be used for supplying oxygen or oxygen enriched air to the patient. Many nasal masks include one or more fixed vent passages or ports. The vent ports are provided to permit carbon dioxide to be purged from the mask. Carbon dioxide is introduced by the patient during the exhalation phase of the patient's breathing cycle. Venting the carbon dioxide prevents the carbon dioxide from being recirculated back to the patient during the inhalation phase of the patient's breathing cycle. The vent ports may be calibrated to provide a continuous but limited vent path through which may flow exhaled air and a portion of the positive pressure air.

The vent ports are frequently located in nasal masks near a bottom of the mask between a pressurized air inlet port and a portion of a facial seal that extends between the nose and the upper lip. This locates the vent ports adjacent the patient's nostrils so that exhaled air is directed towards the vent ports. The vent ports typically have been angled to direct vented air downwardly and slightly away from the patient. The direction in which air is exhausted is determined by the design of the mask and the location of the vent ports. Vent ports are typically arranged to accommodate average users. However, the arrangement of typical vent ports may not be optimal for some patients. Depending on how the patient sleeps, air exhausted from the vents may be directed at the patient or may be deflected, for example, by a pillow towards the patient, causing patient discomfort. If the patient is made uncomfortable by the vented air, there is a risk that the patient will not comply with the prescribed therapy.

A vent port arrangement is needed which reduces the risk that patients will suffer discomfort from vented air and thus encourages patients to comply with a prescribed therapy.

SUMMARY OF THE INVENTION

The present invention is directed towards a nasal mask for use in respiratory a therapy. The mask is provided with one or more vent ports which are adjustable for directing vented air in a direction which is most comfortable to the patient. By providing adjustable vent ports, the patient can adjust the direction of the vented air to a position that best accommodates the patient.

Each vent port can be in the form of a passage in a member which is mounted to rotate in an opening through the mask. The member may be rotated in the opening to change the direction of air flowing through the passage or passages. The member may be designed to rotate about a fixed axis relative to the mask, or it may be spherical and designed to rotate in any direction. Preferably, a knob or tab is provided for grasping to facilitate manually adjusting the vent port orientation.

Accordingly, it is an object of the invention to provide an adjustable vent port arrangement for nasal masks of the type used for treating sleep apnea and other respiratory disorders with the application of a positive pressure to the patient's airway.

Various other objects and advantages of this invention will become apparent to those skilled in the art from the following detailed description of the preferred embodiment, when read in light of the accompanying drawings.

DETAILED DESCRIPTION OF THE PREFERRED EMBODIMENT

Figure 1:
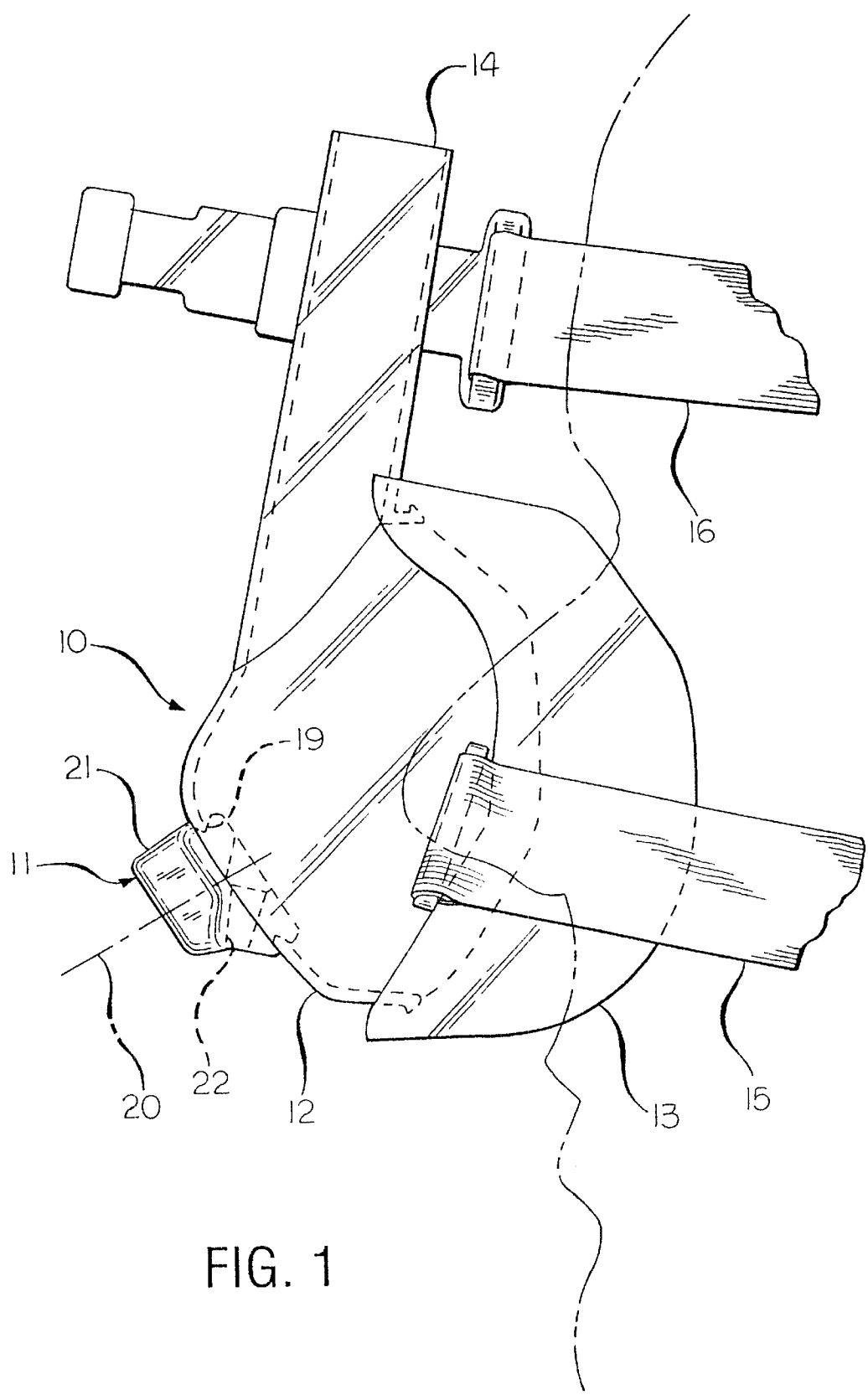
FIG. 1 is an environmental side elevational view of a nasal mask including an adjustable exhaust port member according to a first embodiment of the invention.

Referring to FIG. 1 of the drawings, a mask 10 is shown having a vent or exhaust port member 11 according to the invention. The illustrated mask 10 has a body 12 and resilient facial seal 13 supported by the body 12. The seal 13 is shaped and sufficiently flexible to seal against a patient's face around the nose. The seal 13 may be as illustrated, or of other known designs. For example, the seal 13 may be of the type having a thin flappable seal. Alternatively, the seal 13 may be of the type having a partially inflated tube or of the type filled with a gel like material which flows under pressure to conform to the face. The body 12 includes a pressurized air inlet port 14 which may be in the form of a tube which extends upwardly along the patient's forehead, as shown, or it may have any other known arrangement. A flexible hose (not shown) from a suitable breathing gas source (also not shown), such as a CPAP blower, is connected to the air inlet port 14. Conventional headgear is used to secure the mask to the patient. The headgear may include, for example, one or more straps 15 secured to the mask body 12 and/or a strap 16 which is connected to a tube forming the air inlet port 14 for providing support adjacent the connection to the air hose.

Figure 4:
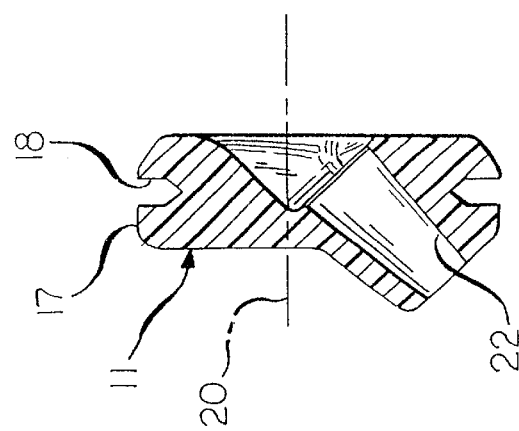
FIG. 4 is a cross sectional view as taken along line 4—4 of FIG. 3.
Figure 3:
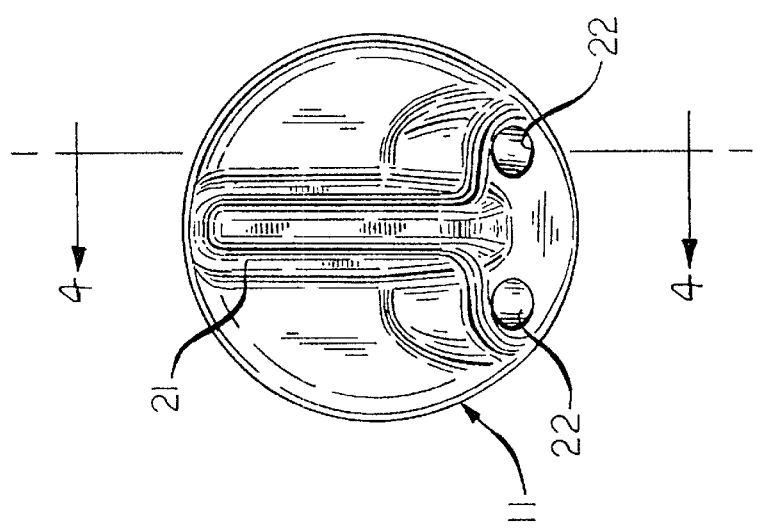
FIG. 3 is a front view of the exhaust port member of FIG. 2.
Figure 2:
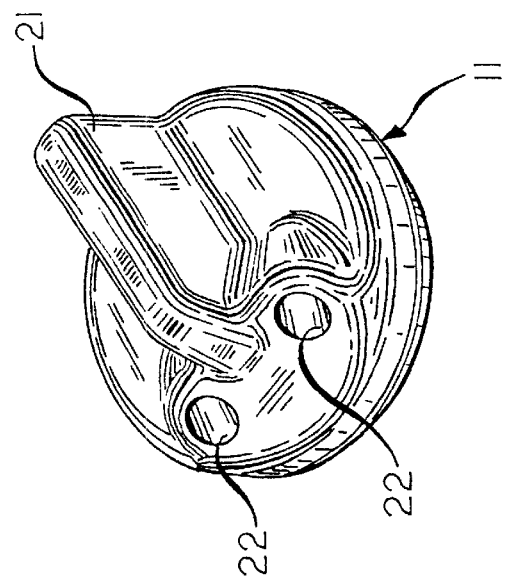
FIG. 2 is a bottom perspective view of the exhaust port member in the nasal mask of FIG. 1.

Referring to FIGS. 1–4, the exhaust port member 11 is shown as having a generally circular perimeter 17 with a recessed or reduced diameter annular groove 18 formed in the perimeter 17, as shown in FIG. 4. A circular opening 19 is formed in the mask body 12 for receiving the exhaust port member 11. Preferably, the exhaust port member 11 is made of a silicone elastomer or of another flexible material to allow the member 11 to deform during the insertion of the member 11 into the opening 19 in the mask body 12. Alternatively, the exhaust port member 11 may be nonflexible and the mask body 12 may be flexible to deform during the insertion of the member 11 into the opening 19 in the mask body 12. The groove 18 and the opening 19 are preferably sized to ensure a proper seal between the mask body 12 and the member 11 and to provide sufficient friction to minimize unintentional rotation of the member 11, while permitting the member 11 to be manually rotated about an axis of rotation 20, shown in FIG. 4. A tab or knob 21 is provided on the exhaust port member 11 to facilitate manual rotation of the exhaust port member 11.

At least one and preferably two vent ports 22 extend through the exhaust port member 11 at a predetermined angle relative to the axis of rotation 20. The vent ports 22 are formed with a predetermined size for providing a desired air flow at a predetermined pressure without unduly reducing the pressure of the air applied to the patient. Preferably, the vent ports 22 are shaped to minimize the noise level of the exhaust air exiting from the ports 22.

The angle of the vent ports 22 relative to the axis 20 may be varied with the orientation of the member 11 relative to the patient. As illustrated in FIG. 1, the vent ports 22 may be angled and the exhaust port member 11 oriented to direct the exhaust air downwardly and slightly away from the patient. When the exhaust port member 11 is rotated 180°, the vent ports 22 will direct the exhaust air upwardly and away from the patient. It should be noted that regardless of the orientation of the exhaust port member 11, the magnitude of the air flow passing through the vent ports 22 will remain constant for a given mask pressure.

Figure 5:
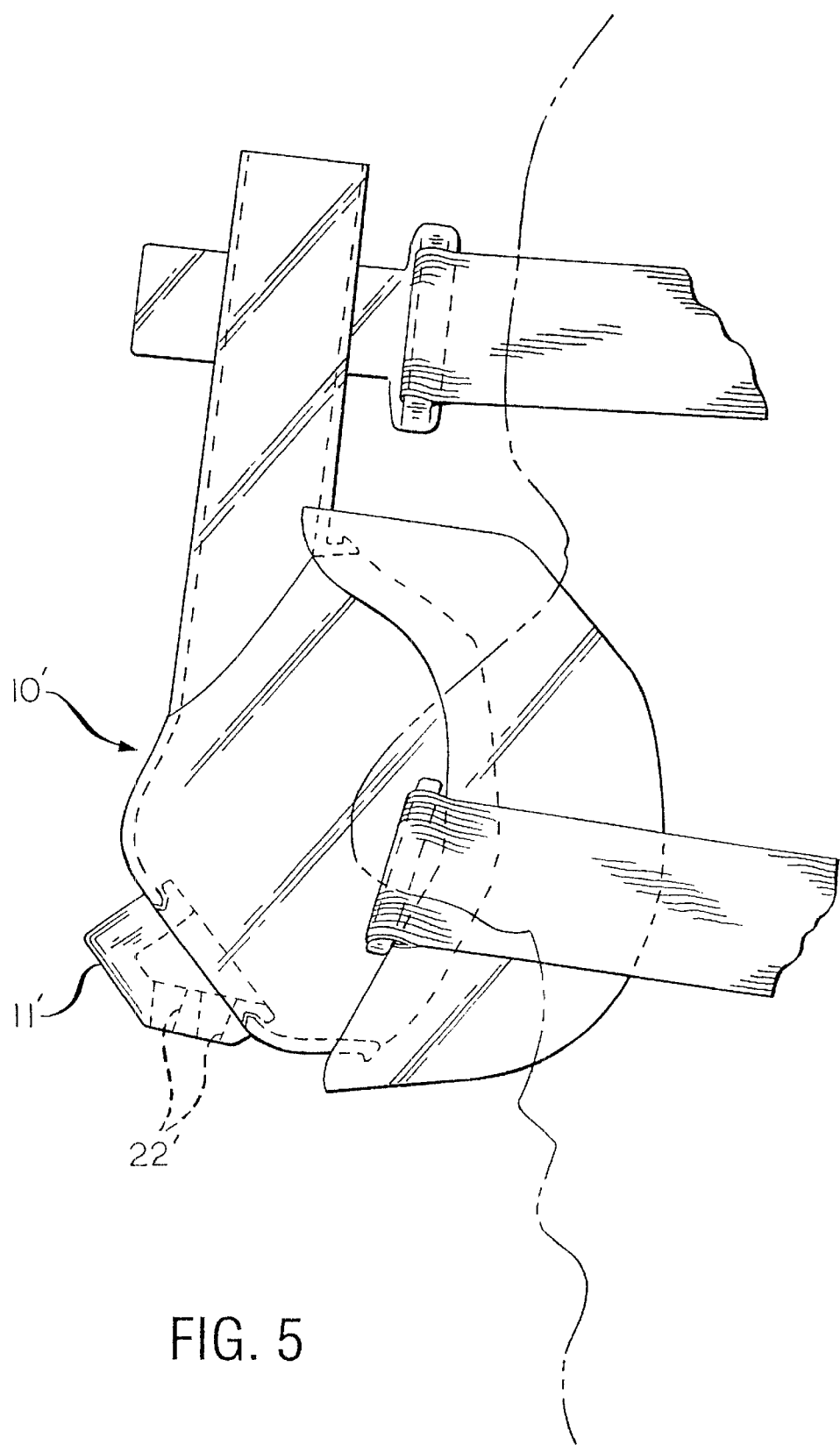
FIG. 5 is an environmental side elevational view of a nasal mask including an adjustable exhaust port member according to a modified embodiment of the invention.
Figure 8:
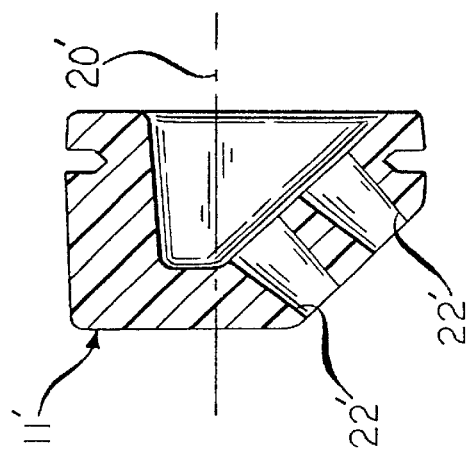
FIG. 8 is a cross sectional view as taken along line 8—8 of FIG. 7.
Figure 7:
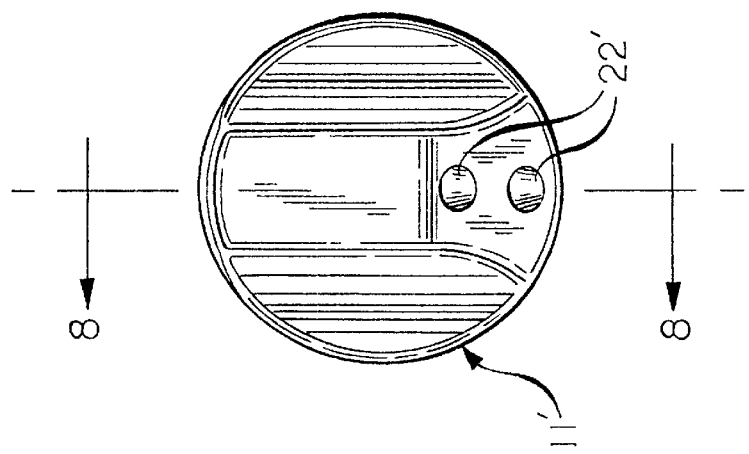
FIG. 7 is a front view of the exhaust port member of FIG. 6.
Figure 6:
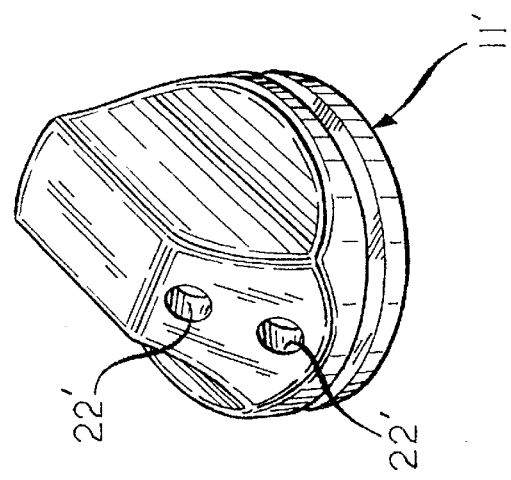
FIG. 6 is a bottom perspective view of the exhaust port member in the nasal mask of FIG. 5.

It will be appreciated that various modifications and changes may be made to the above-described preferred embodiment without departing from the scope of the invention. For example, in FIG. 5 there is illustrated a nasal mask 10' similar to the nasal mask 10 of FIG. 1, except that the rotatable exhaust port member 11' (also shown in FIGS. 6–8) has been modified by spacing the vent ports 22' in a radial direction from the axis of rotation 20'. In FIGS. 1–4, the vent ports are spaced apart on a circumference on the exhaust port member 11.

Figure 9:
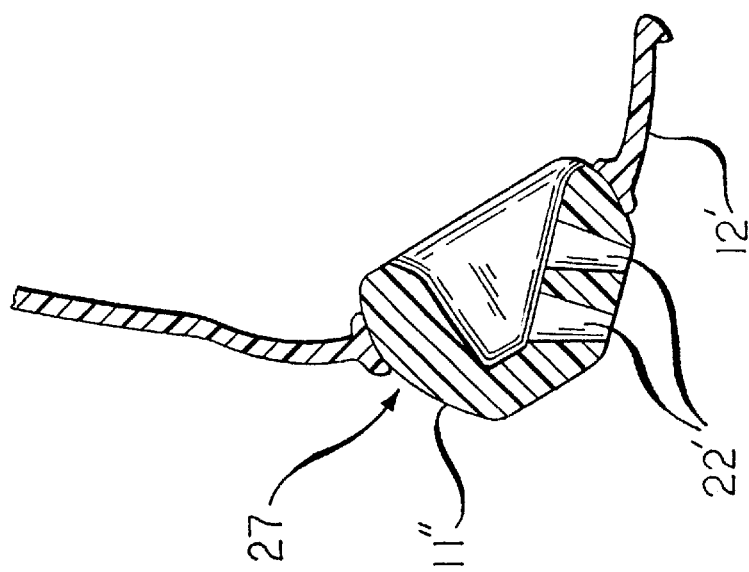
FIG. 9 is an environmental sectional view of an exhaust port member according to another embodiment of the invention.

Another exhaust port member 11" may be spherical, as shown in FIG. 9. The spherical member 11" may be mounted to rotate in a spherical socket 27 in the mask body 12'. The member 11" and the socket 27 are preferably sized to ensure a proper seal between the member 11" and the mask body 12' and to provide sufficient friction to minimize unintentional movement of the member 11", while permitting the member 11" to be manually adjusted. The orientation of the vent ports 22" may be adjusted to direct exhaust air in any desired direction. This differs from the exhaust port members 11, 11' shown in FIGS. 1–8, which have been illustrated as rotating about axes 20, 20'.

Figure 10:
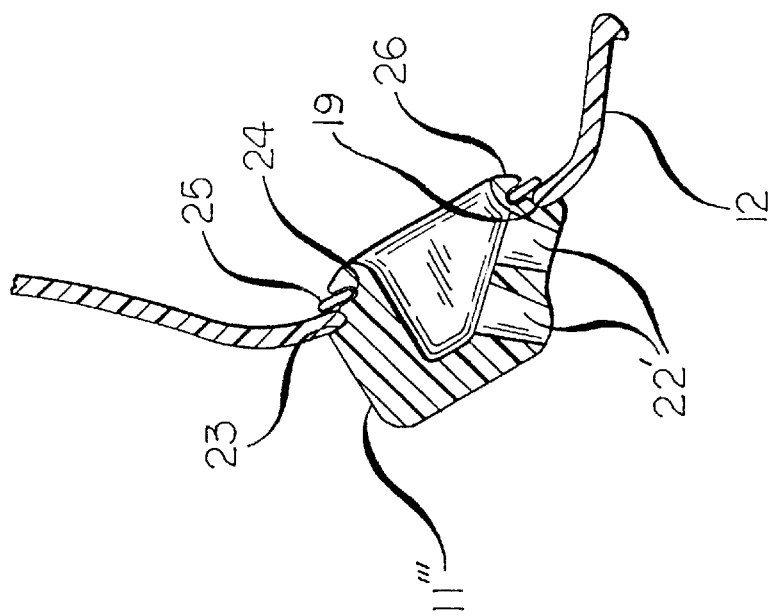
FIG. 10 is an environmental sectional view of an exhaust port member according to yet another embodiment of the invention.

Yet another exhaust port member 11'" is shown in FIG. 10. This exhaust port member 11'" is provided with a shoulder 23 which is adapted to abut an outer portion of the mask body 12 about the opening 19 in the mask body 12. An annular groove 24 is disposed adjacent the opening 19 inside the mask body 12. The groove 24 is adapted to receive a retainer 25. The retainer 25 may be as illustrated, or other known designs. For example, the retainer 25 may be a C-clip. Alternatively, the retainer 25 may be an O-ring. The retainer may be of any known material, such as metal or plastic.

The retainer 25 holds the exhaust port member 11'" in the opening 19 in the mask body 12 with sufficient friction to minimize unintentional movement of the member 11'", while permitting the member 11'" to be manually rotated. For example, the groove 24 and the retainer 25 are preferably sized so that the retainer 25 snugly fits within the groove 24. Moreover, the space between the shoulder 23 and the retainer 25 is sized within the close tolerance of the portion of the mask body 12 about the opening 19.

The exhaust port member 11'" may be provided with a chamfered surface 26 which terminates at the groove 24. The retainer 25 deforms as it progresses along the surface 26 towards the groove 24. Upon reaching the groove 24, the retainer 25 snaps tightly into the groove 24 to secure the exhaust port member 11'" to the mask body 12.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. In a nasal mask for applying a positive air pressure to the airway of a patient, said mask having a body, a facial seal adapted to seal to a patient's face around the patient's nose, and a pressurized air inlet port, an improvement comprising an exhaust port member mounted on said mask body to rotate relative to said mask body about an axis of rotation, said exhaust port member having at least one exhaust air port for venting air from said mask during use by a patient, and wherein said at least one exhaust air port is arranged to direct vented air at an angle relative to said axis of rotation.

2. A nasal mask according to claim 1, and wherein said at least one exhaust air port comprises two exhaust air ports.

3. A nasal mask according to claim 1, and wherein said exhaust port member is formed from a resilient material and has a perimeter forming a reduced diameter annular groove, and wherein said mask body extends into said annular groove and is frictionally engaged by said exhaust port member to form a seal between said mask body and said exhaust port member while permitting said exhaust port member to be manually rotated relative to said mask body.

4. A nasal mask according to claim 3, and wherein said exhaust port member is formed from a silicone elastomer.

5. A nasal mask according to claim 1, and wherein said exhaust port member includes a tab located to facilitate manual rotation of said exhaust port member relative to said mask body.

6. A nasal mask according to claim 1 wherein said exhaust port member is spherical and said mask body has a spherical socket for receiving said exhaust port member so that said exhaust port member is adjustable relative to said mask body.

7. A nasal mask according to claim 1 wherein said exhaust port member has a shoulder abutting an outer portion of said mask body and a groove disposed inside said mask body for receiving a retainer for securing said exhaust port member to said mask body.

8. A nasal mask for applying a positive air pressure to the airway of a patient, said mask comprising:

a body including a pressurized air inlet port;

a facial seal supported by said mask body and adapted to seal to a patient's face around the patient's nose; and an exhaust port member mounted on said mask body to rotate relative to said mask body about an axis of rotation, said exhaust port member having at least one exhaust air port for venting air from said mask during use by a patient, and wherein said at least one exhaust air port is arranged to direct vented air at an angle relative to said axis of rotation.

9. A nasal mask according to claim 8 wherein said exhaust air port comprises two exhaust air ports.

10. A nasal mask according to claim 8 wherein said exhaust port member is formed from a resilient material and has a perimeter forming a recessed annular groove, and wherein said mask body extends into said annular groove and is frictionally engaged by said exhaust port member to form a seal between said mask body and said exhaust port member while permitting said exhaust port member to be manually rotated relative to said mask body.

11. A nasal mask according to claim 10 wherein said exhaust port member is formed from a silicone elastomer.

12. A nasal mask according to claim 8 wherein said exhaust port member includes a tab located to facilitate manual rotation of said exhaust port member relative to said mask body.

13. A nasal mask according to claim 8 wherein said exhaust port member is spherical and said mask body has a spherical socket for receiving said exhaust port member so that said exhaust port member is adjustable relative to said mask body.

14. A nasal mask according to claim 8 wherein said exhaust port member has a shoulder abutting an outer portion of said mask body and a groove disposed inside said mask body for receiving a retainer for securing said exhaust port member to said mask body.

15. A nasal mask for applying a positive air pressure to the airway of a patient, said mask comprising:

a body including a pressurized air inlet port and a circular opening in said mask body;

a resilient facial seal supported by said mask body, said seal being shaped and sufficiently flexible to seal against a patient's face around the patient's nose; and an exhaust port member having a circular perimeter with a recessed annular groove formed in said perimeter, said exhaust port member being inserted in said opening in said mask body so that said mask body extends into said annular groove, said groove and said opening being sized to ensure a proper seal between said mask body and said exhaust port member and to provide sufficient friction to minimize unintentional rotation of said exhaust port member while permitting said exhaust port member to be manually rotated about an axis of rotation, said exhaust port member having a plurality of exhaust air ports at a predetermined angle relative to the axis of rotation for venting air from said mask during use by a patient.

16. A nasal mask according to claim 15 wherein said air inlet port is in the form of a tube adapted to extend upwardly along the patient's forehead.

17. A nasal mask according to claim 15 wherein said exhaust port member is made of a silicone elastomer to allow said member to deform during the insertion of said member into said opening in said mask body.

18. A nasal mask according to claim 15 wherein said exhaust port member is provided with a tab to facilitate manual rotation of said exhaust port member.

\* \* \* \* \*